United States Patent [19] [11] 4,179,335
Long et al. [45] Dec. 18, 1979

[54] THERMOSTABLE LACTASE DERIVED FROM *BACILLUS COAGULANS*

[75] Inventors: Margaret E. Long; Chin K. Lee, both of Winston-Salem, N.C.

[73] Assignee: R. J. Reynolds Tobacco Company, Winston-Salem, N.C.

[21] Appl. No.: 660,094

[22] Filed: Feb. 23, 1976

Related U.S. Application Data

[63] Continuation-in-part of Ser. No. 529,329, Dec. 4, 1974, abandoned.

[51] Int. Cl.² ............................................. C12D 13/10
[52] U.S. Cl. .................................... 435/99; 435/207; 435/832
[58] Field of Search ............... 195/31 R, 62, 65, 66 R, 195/11

[56] References Cited

U.S. PATENT DOCUMENTS 3,816,259  6/1974  Collinge et al. ...................... 195/62

OTHER PUBLICATIONS

P. J. Anema, Biochimica et Biophysica Acta, 89, 1964, pp. 495–502.
Wierzbicki et al., Journal of Dairy Science, vol. 56 (1), pp. 26 to 32 (1973).

*Primary Examiner*—Lionel M. Shapiro
*Attorney, Agent, or Firm*—Neuman, Williams, Anderson & Olson

[57] ABSTRACT

A thermostable lactase is obtained by cultivation of a member of the genus Bacillus in a suitable nutrient medium. The resulting lactose-containing cells or the cell-free enzyme are useful for the hydrolysis of lactose in a variety of substrate media.

6 Claims, No Drawings

THERMOSTABLE LACTASE DERIVED FROM *BACILLUS COAGULANS*

SUMMARY OF THE INVENTION

This application is a continuation-in-part of application Ser. No. 529,329 filed Dec. 4, 1974, now abandoned.

This invention relates to a process for producing lactase from a heat-tolerant organism belonging to the genus Bacillus. The lactase exhibits improved thermal stability in comparison with Bacillus-derived lactase reported in the literature and it is effective for hydrolyzing lactose in milk, milk-derived products and other lactose-containing media.

BACKGROUND OF THE INVENTION

There has been considerable interest in recent years in developing methods for reducing lactose levels in milk and milk-derived products. This interest has been heightened by recent evidence that a large percentage of the human population suffers from a lactase deficiency which is either an inherited trait or a result of the aging process. Such lactase deficiencies lead to intestinal disorders when dietary levels of lactose are high. Moreover, a similar lactose intolerance has also been observed in certain domestic animals.

The hydrolysis of lactose in milk and milk-derived products to produce glucose and galactose is an attractive goal not only because it would solve the lactose intolerance problem but it would also increase the sweetness of the products and reduce so-called sandy textures in certain milk-derived products caused by lactose crystallization. Those working in the field have long appreciated the desirability of effecting this hydrolysis by the use of lactase. In spite of the fact that lactase occurs rather widely in nature and is produced by many microorganisms, the use of lactase in the commercial production of milk and milk-derived products have been very limited. One reason for the limited commercial use of lactase is that many of the common lactases such as those derived from yeast exhibit optimum enzyme activity at temperatures which are also conducive to bacterial growth. Accordingly, there has been increasing interest in finding a lactase having a high degree of heat stability. Such a heat stable lactase would permit lactose hydrolysis to be carried out under conditions that are unfavorable for growth of certain bacteria which are commonly present in milk or milk-derived products. One such lactase derived from *Streptomyces coelicolor* has recently been described in U.S. Pat. No. 3,816,259. It is not clear at this time, however, whether lactase from *S. coelicolor* can be used with impunity because certain members of that species have been reported to produce antibiotics.

The production of lactase by members of the genus Bacillus has been previously reported. P. J. Anema has reported in Biochim. Biophys. Acta 89 (3), 495–502 (1964) the isolation of lactase from *B. subtilis*. Lactase from *B. megaterium* was described by S. R. Rohlfing and I. P. Crawford in J. Bacteriology 92 (4), 1258–9 (1966). Neither of these organisms, however, is regarded as heat-tolerant and the lactase produced by them must generally be used at temperatures below about 50° C. in order to retain useful enzyme activity for extended periods of time.

DETAILED DESCRIPTION

A preferred organism for use in accordance with this invention has been isolated from a soil sample. Culturing the organism in a suitable nutrient medium containing lactose produces the desired lactase intracellularly. Characterization of this culture has been carried out and it has been identified as falling within the species *Bacillus coagulans* according to the classification given in Bergey's Manual of Determinative Bacteriology, 7th edition. This organism is included in the culture collection of the U.S.D.A. Northern Regional Research Laboratory under the designation NRRL B-8100. The taxonomic properties of this strain are shown in Table 1.

TABLE 1

A. Morphological Characteristics
  1. Vegetative Rods: Less than 0.9 micron in diameter varying in length generally up to 5.0–6.0 microns. Some filaments. Not in chains. Gram positive, staining uniformly. Motile.
  2. Sporangia: Generally not swollen but occasional swollen sporangia may be found.
  3. Spores: 0.9 by 1.2 to 1.5 microns, ellipsoidal, subterminal to terminal.

B. Cultural Characteristics
  1. Gelatin agar streak plate—No hydrolysis.
  2. Agar colonies—Opaque, small, round. Not distinctive.
  3. Agar slants—Scant to moderate growth. Flat, smooth, opaque.
  4. Glucose agar slant—Growth heavier than on nutrient agar. Smooth white.
  5. Glucose asparagine agar slants—No growth at 24 hours. Moderate growth at 48 hours.
  6. Proteose peptone acid agar slants—Good growth, better than on nutrient agar.
  7. Soybean agar slants—Growth moderate, slightly heavier than on nutrient agar.
  8. Stock culture agar slants—Growth scant at 24 hours, as good as nutrient agar at 48 hours.
  9. Broth—Growth poor after 24 hours.
  10. Sodium chloride broth—No growth in 7% sodium chloride.
  11. Milk agar streak plate—No hydrolysis.
  12. Potato—Scant, dry, wrinkled.

C. Physiological Characteristics
  1. Using peptone as the nitrogen source, the organism produced acid but no gas from glucose, lactose, arabinose, xylose, mannitol and maltose. Neutral reaction from sucrose and glycerol.
  2. The pH of glucose broth is 5.0 or less in seven days.
  3. Citrates not utilized.
  4. Tomato yeast milk curdled in 24 hours at 45° C.
  5. Nitrites not produced from nitrates.
  6. Voges-Proskauer test is negative. pH of Voges-Proskauer broth is 4.2.
  7. Hydrolysis of starch—Positive.
  8. Catalase—Positive.
  9. No growth in nitrate medium under anaerobic conditions. Growth in glucose broth under anaerobic conditions produces a pH less than 5.2 in seven days.
  10. Aerobic, facultatively anaerobic.
  11. Minimum temperature for growth is 25° C. Maximum temperature for growth is 60° C. Optimum growth occurs at 45°–50° C.

As indicated under the physiological characteristics listed in Table 1, the Bacillus organism disclosed herein exhibits optimum growth at temperatures of about 45°–50° C. and is, therefore, regarded as a heat-tolerant organism in comparison with other Bacilli which display optimum growth at about 37° C. A heat-tolerant Bacillus organism is defined herein as one which exhibits optimum growth at temperatures of about 45° C. and above.

The pH optimum of the lactase produced by this organism was determined by assaying whole cells in the presence of o-nitrophenyl-β-galactoside (ONPG) as the substrate. The procedure used was essentially that of J. Lederberg as described in J. Bacteriology 60, 381 (1950). Cells were first treated with toluene, a phosphate buffer was used and the assay temperature was 37° C. Lactase activity was observed in the range of about pH 4.5 to 8.0 with optimum activity occurring at about pH 6.0.

Stability of the lactase enzyme produced by *B. coagulans* was evaluated by using ONPG as the substrate in a modification of the Lederberg procedure. For this evaluation washed cells were suspended in 0.05 M phosphate buffer at pH 7.0 in the presence of the ONPG substrate. The suspension was then maintained at 60° C. for four days with samples being periodically withdrawn for determining the lactase activity remaining. The temperature of this stability test was selected as approximating the temperature levels used in low temperature pasteurization. Results of the test are shown in Table 2.

TABLE 2

| Time in Hours | Lactase Activity as Percent of Original Activity |
|---|---|
| 0 | 100 |
| 21 | 92 |
| 45 | 51 |
| 71 | 36 |
| 99 | 20 |

The lactase produced by *Bacillus coagulans* exhibits useful enzyme activity up to about 70° C. Optimum activity appears to occur at temperatures of 60° to 65° C. The particular temperature selected for effecting lactose hydrolysis by the use of this enzyme will depend somewhat on the substrate medium involved. Generally speaking, however, temperatures between about 45° and 65° C. are preferred.

A typical medium for cultivating *Bacillus coagulans* to produce lactase is as follows:

| | |
|---|---|
| Proteose peptone | 1.0% |
| Yeast extract | 1.0% |
| Potassium dihydrogen phosphate | 0.8% |
| Lactose (sterilized separately) | 2.0% |
| pH | 6.0 |

Other nutrient media may be employed including other carbohydrate sources such as glucose and galactose. Cultures are incubated on a rotary shaker for 48 hours at 45° C. At the end of the incubation period toluene is added to the broth (0.5% on a volume per volume basis) and the mixture is agitated for 30 minutes. Cells are then recovered by flocculation techniques described in U.S. Pat. No. 3,821,086 and the flocculated cell aggregate thereby obtained is dried at 55° C. Lactase activity of the dried aggregate particles is 38.5 units per gram where a unit is defined as the quantity of enzyme necessary to produce one micromole of dextrose per minute under the assay conditions. The assay method used for this determination is that of Weetall et al. as published in Biotechnology and Bioengineering 16, 295 (1974).

The effectiveness of the lactase produced by *Bacillus coagulans* was demonstrated by the hydrolysis of lactose in a sweet whey feed stock. The organism was cultivated and the cells were recovered as described above. The dried aggregate particles were sieved and 5 grams of the 16–20 mesh portion were hydrated in a 50 percent lactose solution buffered at pH 7.0 with a 0.05 M phosphate buffer. The hydrated particles were then packed into a small glass column that was maintained at a temperature of 60° C. Through this packed column was passed continuously an aqueous solution containing 70 grams of a commercial dried sweet whey powder per liter, the solution being buffered with 0.05 M phosphate at pH 7.0. The feed solution contained approximately 5 percent by weight lactose based on the lactose content of the sweet whey and 100 milligrams per liter of methyl p-hydroxybenzoate was added as a preservative. Flow rate through the column was maintained at 375 milliliters per day and the degree of lactose hydrolysis was monitored daily by routine analysis. Initial degree of lactose hydrolysis was found to be 90 percent. After 3 weeks of continuous operation the degree of lactose hydrolysis had decreased to 80 percent.

It will be appreciated that the lactase produced in accordance with this invention may be used for either batch or continuous treatment of lactose substrate media. Moreover, the lactase may be utilized by direct use of the cells or it may be used in the form of cell-free enzyme by applying techniques known to those skilled in the art. Any further modifications falling within the scope of the appended claims are to be considered as part of this invention.

What is claimed is:

1. A process for producing a lactase having improved thermal stability which comprises cultivating an organism belonging to the species *Bacillus coagulans* in a nutrient medium under conditions suitable for producing said lactase and recovering the lactase thereby produced, said lactase retaining a substantial amount of activity for at least one hour at 60° C. as determined by assaying lactase activity associated with washed cells of said organism suspended in a 0.05 M phosphate buffer at pH 7.0 in the presence of o-nitrophenyl-β-galactoside.

2. The process of claim 1 wherein the organism is cultivated in the nutrient medium at a temperature of at least 40° C.

3. A process for hydrolyzing lactose to produce glucose and galactose which comprises contacting lactose with a lactase under lactose-hydrolyzing conditions and recovering a product containing glucose and galactose wherein said lactase is derived from an organism belonging to the species *Bacillus coagulans* and exhibits activity in the range of about pH 4.5 to 8.0 as determined by assaying whole cells of said organism in the presence of o-nitrophenyl-β-galactoside, said lactase retaining a substantial amount of activity for at least one hour at 60° C. as determined by assaying lactase activity associated with washed cells of said organism suspended in a 0.05 M phosphate buffer at pH 7.0 in the presence of o-nitrophenyl-β-galactoside.

4. A process according to claim 3 in which lactose is contacted with the lactase at a pH between 4.8 and 8.0 and at a temperature between about 45° and 65° C.

5. A process for producing a lactase having improved thermal stability which comprises cultivating the organism, *Bacillus coagulans* NRRL B-8100, in a nutrient medium under conditions suitable for producing said lactase and recovering the lactase thereby produced.

6. A process for hydrolyzing lactose to produce glucose and galactose which comprises contacting lactose with a lactase derived from the organism, *Bacillus coagulans* NRRL B-8100, under lactose-hydrolyzing conditions and recovering a product containing glucose and galactose.

* * * * *

UNITED STATES PATENT AND TRADEMARK OFFICE
CERTIFICATE OF CORRECTION

PATENT NO. : 4,179,335

DATED : December 18, 1979

INVENTOR(S) : Margaret E. Long and Chin K. Lee

It is certified that error appears in the above-identified patent and that said Letters Patent are hereby corrected as shown below:

In the Abstract, line 3, "lactose" should be -- lactase --

Column 3, line 29, "of" should be -- for --

Column 5, line 2, "4.8" should be -- 4.5 --

Signed and Sealed this

First Day of April 1980

[SEAL]

Attest:

SIDNEY A. DIAMOND

Attesting Officer

Commissioner of Patents and Trademarks